United States Patent
Sugihara

(10) Patent No.: US 9,874,514 B2
(45) Date of Patent: Jan. 23, 2018

(54) ATOMIC ABSORPTION SPECTROPHOTOMETER AND SIGNAL VOLTAGE OPTIMIZATION METHOD USED BY THE SAME

(71) Applicant: Shimadzu Corporation, Kyoto-shi, Kyoto (JP)

(72) Inventor: Kazuo Sugihara, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 253 days.

(21) Appl. No.: 14/437,754

(22) PCT Filed: Nov. 5, 2012

(86) PCT No.: PCT/JP2012/078603
§ 371 (c)(1),
(2) Date: Apr. 22, 2015

(87) PCT Pub. No.: WO2014/068781
PCT Pub. Date: May 8, 2014

(65) Prior Publication Data
US 2015/0293014 A1    Oct. 15, 2015

(51) Int. Cl.
*G01J 3/30* (2006.01)
*G01N 21/31* (2006.01)
*G01N 21/27* (2006.01)

(52) U.S. Cl.
CPC ......... *G01N 21/3103* (2013.01); *G01N 21/27* (2013.01)

(58) Field of Classification Search
CPC ........................... G01N 21/3101; G01N 21/27
(Continued)

(56) References Cited

U.S. PATENT DOCUMENTS 6,043,880 A * 3/2000 Andrews ............... G01N 21/64
                                                      250/361 C
6,809,804 B1 * 10/2004 Yount ............... G01N 15/1459
                                                      250/214 DC
(Continued)

FOREIGN PATENT DOCUMENTS

JP    52-055686 A    5/1977
JP    09-089764 A    4/1997
(Continued)

OTHER PUBLICATIONS

International Search Report for PCT/JP2012/078603 dated Feb. 5, 2013 [PCT/ISA/210].

*Primary Examiner* — Hina F Ayub
(74) *Attorney, Agent, or Firm* — Sughrue Mion, PLLC

(57) ABSTRACT

There are provided an atomic absorption spectrophotometer capable of effectively preventing saturation of a signal voltage of a detector at the time of measurement, and a signal voltage optimization method used by the same. Test measurement of a sample is performed in a state where a preset value is taken as a set value of the signal voltage of the detector. The set value of the signal voltage of the detector corresponding to the sample is optimized based on the signal voltage of the detector at the time of the test measurement of the sample. In this manner, by optimizing the set value of the signal voltage of the detector corresponding to the sample through test measurement using the actual sample, saturation of the signal voltage of the detector at the time of measurement may be effectively prevented.

10 Claims, 3 Drawing Sheets

(58) Field of Classification Search
USPC .......................................................... 356/311
See application file for complete search history.

(56) References Cited

U.S. PATENT DOCUMENTS

| | | | |
|---|---|---|---|
| 2002/0180970 A1* | 12/2002 | Hammer | ................... G01J 3/02 |
| | | | 356/330 |
| 2003/0160184 A1 | 8/2003 | Curry et al. | |
| 2004/0223153 A1* | 11/2004 | Sakai | ..................... G01N 21/74 |
| | | | 356/319 |
| 2009/0316148 A1 | 12/2009 | Minato | |
| 2010/0073675 A1* | 3/2010 | Harada | ................. G01N 21/274 |
| | | | 356/317 |

FOREIGN PATENT DOCUMENTS

| | | | |
|---|---|---|---|
| JP | 2001-153799 A | 6/2001 | |
| JP | 2004-325341 A | 11/2004 | |
| JP | 2007-010314 A | 1/2007 | |

\* cited by examiner

ATOMIC ABSORPTION SPECTROPHOTOMETER AND SIGNAL VOLTAGE OPTIMIZATION METHOD USED BY THE SAME

CROSS REFERENCE TO RELATED APPLICATIONS

This application is a National Stage of International Application No. PCT/JP2012/078603 filed Nov. 5, 2012, the contents of all of which are incorporated herein by reference in their entirety.

TECHNICAL FIELD

The present invention relates to an atomic absorption spectrophotometer for causing measurement light to pass through atomic vapor generated by heating and atomizing a sample and detecting the measurement light by a detector to measure absorbance of the sample, and a signal voltage optimization method used by the same.

BACKGROUND ART

An atomic absorption spectrophotometer is provided with an atomizing unit for heating and atomizing a sample. At the atomizing unit, a sample is atomized, thereby generating atomic vapor, and measurement light is radiated in the atomic vapor by a light source. At this time, light of a specific wavelength is absorbed in the atomic vapor, and thus, analysis of the sample may be performed by measuring the absorbance (for example, see Patent Documents 1 and 2).

The measurement light which has passed through the atomic vapor is detected by a detector. The detector may be configured from a photomultiplier tube, for example. An output signal from the detector is amplified by an amplifier, and is then input to a control unit via an A/D converter. At the control unit, the absorbance is measured based on the ratio between the received intensity of measurement light when light is absorbed in the atomic vapor and the received intensity of measurement light when light is not absorbed.

With a general atomic absorption spectrophotometer, light that reaches the detector includes, in addition to the measurement light from the light source as described above, light from outside the device, light occurring at the atomizing unit and the like, for example. As the light occurring at the atomizing unit, light emission from the structure of the atomizing unit accompanying heating, light emission from the sample itself and the like may be cited. Among these light emissions, light emission from the sample itself has a property that the amount of light emission is greater as the concentration of the sample is higher.

With this type of atomic absorption spectrophotometer, depending on the measurement conditions, the amount of light emission from the structure of the atomizing unit accompanying heating may change, and a signal voltage of the detector (detector signal voltage) may exceed the maximum voltage that can be measured. Accordingly, Patent Document 1 proposes a configuration for storing detector signal voltages for all the settable combinations of wavelengths, slit widths, and atomizing temperatures of the atomizing unit. Then, at the time of sample measurement, an amplifier is controlled by an optimum detector signal amplification factor based on the detector signal voltage stored in relation to the wavelength, the slit width, and the atomizing temperature used for the sample measurement.

However, even with the configuration in Patent Document 1, depending on the measurement conditions (wavelength, slit width, flame species, gas flow rate), the detector signal voltage may exceed the maximum voltage that can be measured and accurate measurement is sometimes prevented. Thus, Patent Document 2 proposes a configuration for storing an optimal value of the detector signal voltage for an A/D converter corresponding to a combination of measurement conditions that may be simultaneously set. Then, when measurement conditions are set, a voltage adjustment section or a signal amplifier is adjusted so that the optimal value of a corresponding detector signal voltage is input to the A/D converter.

PRIOR ART DOCUMENTS

Patent Documents

Patent Document 1: JP 2004-325341 A
Patent Document 2: JP 2007-10314 A

SUMMARY OF THE INVENTION

Problems to be Solved by the Invention

As described above, by optimizing the detector signal voltage or the amplification factor by taking measurement conditions into account, measurement may be normally performed in many cases. However, in the case where the concentration of a sample which is the analysis target is unexpectedly high, the amount of light emission from the sample itself may be unexpectedly great. Also, shifting of the optical axis of measurement light with respect to the atomizing unit caused by insufficient adjustment or the like may result in an unexpectedly great amount of light emission from the structure of the atomizing unit.

In the case where the amount of light emission from the sample itself or the structure of the atomizing unit is unexpectedly great as described above, the detector signal voltage may be saturated, and measurement may not be normally performed. A set value of the detector signal voltage may be set low in advance taking into account of saturation of the detector signal voltage, but in this case, there is a problem that the S/N ratio at the time of measurement is reduced and the measurement accuracy is reduced.

The present invention has been made in view of the above circumstances, and has its aim to provide an atomic absorption spectrophotometer capable of effectively preventing saturation of a signal voltage of a detector at the time of measurement, and a signal voltage optimization method used by the same.

Means for Solving the Problems

An atomic absorption spectrophotometer of the present invention is an atomic absorption spectrophotometer for causing measurement light to pass through atomic vapor generated by heating and atomizing a sample and detecting the measurement light by a detector to measure absorbance of the sample, the atomic absorption spectrophotometer comprising: a test measurement execution processing unit for performing test measurement of the sample in a state where a preset value is taken as a set value of a signal voltage of the detector; and a signal voltage optimization processing unit for optimizing, based on the signal voltage of the detector at a time of the test measurement of the sample, the set value of the signal voltage of the detector corresponding to the sample.

According to the configuration described above, by performing test measurement of a sample, the set value of the signal voltage of the detector corresponding to the sample may be optimized based on the signal voltage of the detector at the time of the test measurement. That is, the set value of the signal voltage of the detector corresponding to the sample may be optimized through test measurement using the actual sample.

Therefore, even in a case where the amount of light emission of the sample itself or of the structure of the atomizing unit is unexpectedly great, the set value of the signal voltage of the detector corresponding to the sample may be set to a value according to which the signal voltage is not saturated at the time of actual measurement. Accordingly, saturation of the signal voltage of the detector at the time of measurement may be effectively prevented.

The atomic absorption spectrophotometer preferably further comprises a signal voltage storage unit for storing, in association with the sample, the set value of the signal voltage of the detector optimized by the signal voltage optimization processing unit.

According to the configuration described above, by storing the optimized set value of the signal voltage of the detector in association with a sample, at the time of performing measurement of the same sample, measurement may be performed by reading the set value. Then, the efficiency of measurement may be increased, and also, saturation of the signal voltage of the detector at the time of measurement may be effectively prevented.

In a case where the signal voltage of the detector at a time of the test measurement of the sample is below an upper limit value, the signal voltage optimization processing unit may determine the preset value to be the set value of the signal voltage of the detector corresponding to the sample.

According to the configuration described above, in the case where the signal voltage of the detector is below the upper limit value at the time of test measurement of a sample where a preset value is taken as the set value of the signal voltage of the detector, the preset value may be determined to be a value according to which the signal voltage of the detector will not be saturated at the time of actual measurement, and be determined to be the set value corresponding to the sample.

In a case where the signal voltage of the detector at a time of the test measurement of the sample is at or above an upper limit value, the test measurement execution processing unit may reset the set value of the signal voltage of the detector to a lower value, and perform again the test measurement of the sample. In this case, in a case where the test measurement of the sample is performed several times, the signal voltage optimization processing unit may determine the set value of the signal voltage when the signal voltage of the detector falls below the upper limit value to be the set value of the signal voltage of the detector corresponding to the sample.

According to the configuration described above, in the case where the signal voltage of the detector is at or above the upper limit value at the time of test measurement of a sample where the preset value is taken as the set value of the signal voltage of the detector, the preset value may be determined to be a value according to which the signal voltage of the detector will possibly be saturated, and be reset to a lower value. When the set value of the signal voltage of the detector is reset in this manner, and the test measurement of the sample is performed several times, the set value of the signal voltage at the time of the signal voltage of the detector falling below the upper limit value may be determined to be a value according to which the signal voltage of the detector will not be saturated at the time of actual measurement, and be determined to be the set value corresponding to the sample.

In a case where the set value of the signal voltage of the detector that is reset reaches a lower limit value, the test measurement execution processing unit may end the test measurement of the sample.

According to the configuration described above, in the case where the set value reaches the lower limit value without the signal voltage of the detector falling below the upper limit value when the set value of the signal voltage of the detector is reset and test measurement of a sample is performed several times, the test measurement of the sample may be ended. In such a case, conditions other than the signal voltage of the detector have to be re-examined, and thus, the test measurement of the sample is ended, and other appropriate measures may be taken.

A signal voltage optimization method of an atomic absorption spectrophotometer of the present invention is a method for optimizing a set value of a signal voltage of a detector in the atomic absorption spectrophotometer for causing measurement light to pass through atomic vapor generated by heating and atomizing a sample and detecting the measurement light by the detector to measure absorbance of the sample, the method comprising: a test measurement execution processing step of performing test measurement of the sample in a state where a preset value is taken as the set value of the signal voltage of the detector; and a signal voltage optimization processing step of optimizing, based on the signal voltage of the detector at a time of the test measurement of the sample, the set value of the signal voltage of the detector corresponding to the sample.

The signal voltage optimization method preferably further comprises a signal voltage storage step of storing, in association with the sample, the set value of the signal voltage of the detector optimized in the signal voltage optimization processing step.

In the signal voltage optimization processing step, in a case where the signal voltage of the detector at a time of the test measurement of the sample is below an upper limit value, the preset value may be determined to be the set value of the signal voltage of the detector corresponding to the sample.

In the test measurement execution processing step, in a case where the signal voltage of the detector at a time of the test measurement of the sample is at or above an upper limit value, the set value of the signal voltage of the detector may be reset to a lower value, and the test measurement of the sample may be performed again. In this case, in the signal voltage optimization processing step, in a case where the test measurement of the sample is performed several times, the set value of the signal voltage when the signal voltage of the detector falls below the upper limit value may be determined to be the set value of the signal voltage of the detector corresponding to the sample.

In the test measurement execution processing step, in a case where the set value of the signal voltage of the detector that is reset reaches a lower limit value, the test measurement of the sample may be ended.

Effects of the Invention

According to the present invention, by optimizing the set value of the signal voltage of the detector corresponding to a sample through test measurement using the actual sample, saturation of the signal voltage of the detector at the time of measurement may be effectively prevented.

MODE FOR CARRYING OUT THE INVENTION

Figure 1:
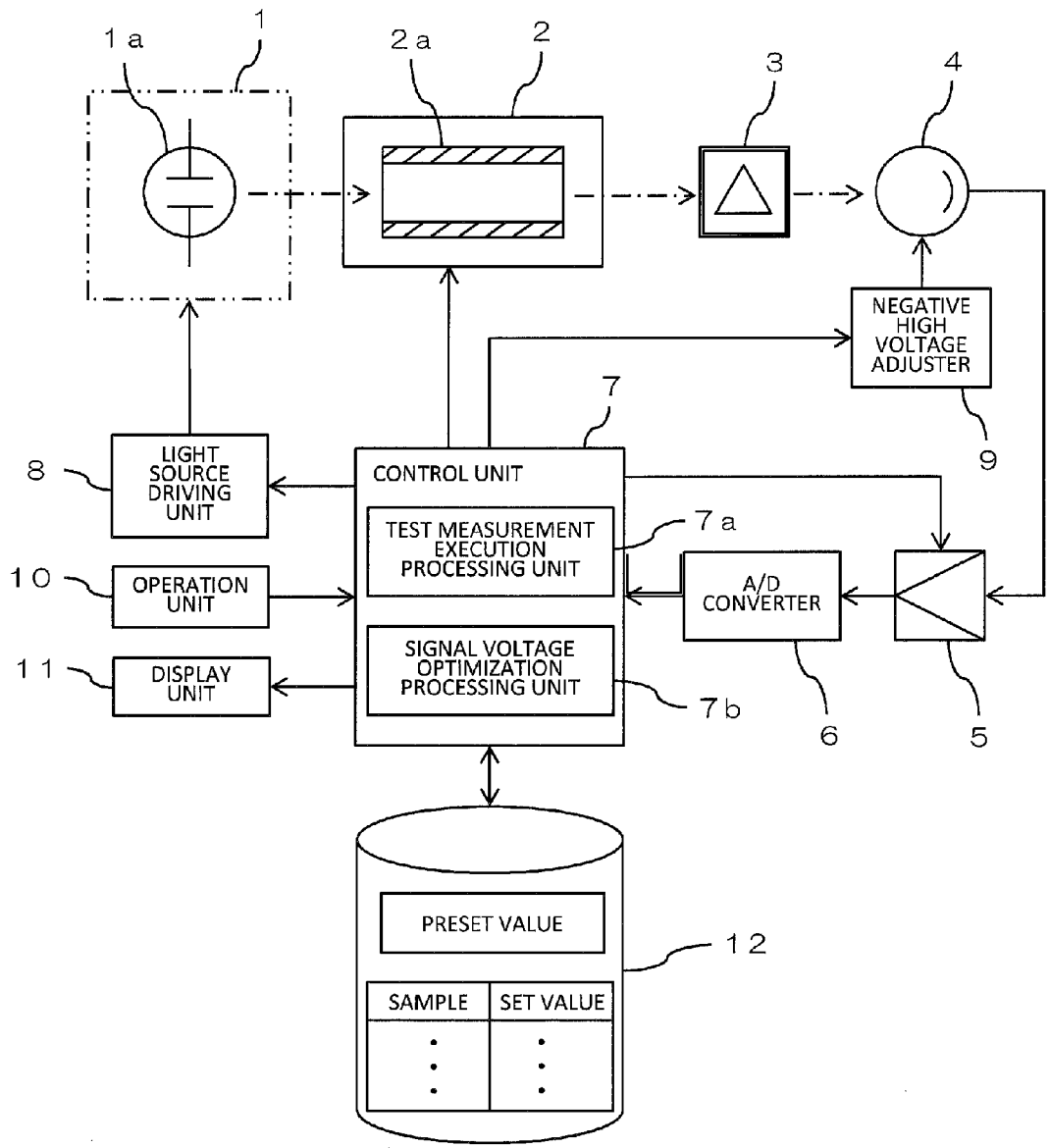
FIG. 1 is a diagram showing a configuration example of an atomic absorption spectrophotometer according to an embodiment of the present invention.

FIG. 1 is a diagram showing a configuration example of an atomic absorption spectrophotometer according to an embodiment of the present invention. This atomic absorption spectrophotometer is a so-called furnace atomic absorption spectrophotometer, and is for generating atomic vapor by heating and atomizing a sample inside a graphite tube $2a$, and measuring the absorbance of the sample by causing measurement light to pass through the atomic vapor.

This atomic absorption spectrophotometer is provided with a light source 1, an atomizing unit 2, a spectroscope 3, a photomultiplier tube 4, an amplifier 5, an A/D converter 6, a control unit 7, a light source driving unit 8, a negative high voltage adjuster 9, an operation unit 10, a display unit 11, a memory 12, and the like.

The light source 1 is provided with a hollow cathode lamp (HCL) $1a$ for radiating measurement light containing a bright line spectrum. The measurement light radiated from the hollow cathode lamp $1a$ passes through the graphite tube $2a$ provided to the atomizing unit 2.

A sample solution is injected into the graphite tube $2a$ from a sample injection port (not shown), and the sample solution is heated by the graphite tube $2a$ through which a large current flows. The sample is thereby atomized, and atomic vapor is generated inside the graphite tube $2a$. The measurement light has the light of a wavelength that is unique to the element contained in the sample greatly absorbed in the process of passing through the atomic vapor in the graphite tube $2a$.

The measurement light which has passed through the atomizing unit 2 enters the spectroscope 3. A diffraction grating is provided to the spectroscope 3, for example, and measurement light diffracted by the diffraction grating enters the photomultiplier tube 4. The photomultiplier tube 4 is an example of a detector for detecting measurement light, and outputs a signal according to the received intensity of the measurement light. The output signal from this photomultiplier tube 4 is amplified by the amplifier 5, and is then converted into a digital signal by the A/D converter 6 and input to the control unit 7.

The control unit 7 is a structure including a CPU (Central Processing Unit), for example, and controls the operation of each unit provided to the atomic absorption spectrophotometer. At the control unit 7, the absorbance of the sample is measured based on the input signal from the A/D converter 6. Specifically, the absorbance is measured based on the ratio between the received intensity of measurement light when light is absorbed in the atomic vapor and the received intensity of measurement light when light is not absorbed.

The atomizing unit 2, the amplifier 5, the light source driving unit 8, the negative high voltage adjuster 9, the operation unit 10, the display unit 11, the memory 12 and the like are electrically connected to the control unit 7. The light source driving unit 8 is for driving the hollow cathode lamp $1a$ provided to the light source 1, and outputs a drive signal to the hollow cathode lamp $1a$ based on a control signal from the control unit 7.

The signal voltage of the photomultiplier tube 4 is dependent on the negative high voltage applied to the photomultiplier tube 4. Accordingly, by adjusting the negative high voltage to be applied to the photomultiplier tube 4 via the negative high voltage adjuster 9, the amplification factor of the signal voltage of the photomultiplier tube 4 may be adjusted. In the present embodiment, adjustment of the signal voltage is enabled by adjusting the amplification factor of the signal voltage of the photomultiplier tube 4 by the negative high voltage adjuster 9 after determining a signal level of a certain degree by circuit switching of the amplifier 5, and by performing control so as to bring the signal voltage closer to a set value (target value).

The operation unit 10 is a structure including a keyboard or a mouse, for example, and an input task may be performed by an operator operating the operation unit 10. The display unit 11 may be configured from a liquid crystal display, for example, and results of processing by the control unit 7 and the like may be displayed on the display unit 11. The memory 12 may be configured from a ROM (Read Only Memory), a RAM (Random Access Memory) and the like, for example.

The control unit 7 functions as a test measurement execution processing unit $7a$, a signal voltage optimization processing unit $7b$ and the like by the CPU executing programs. In the present embodiment, before actually measuring a sample, test measurement of the sample is performed by the test measurement execution processing unit $7a$, and a set value of the signal voltage of the photomultiplier tube 4 corresponding to the sample may be optimized based on the result of the test measurement.

The test measurement execution processing unit $7a$ performs test measurement of the sample in a state where a preset value is taken as the set value of the signal voltage of the photomultiplier tube 4. The preset value is stored in the memory 12, and at the time of test measurement, this preset value is read from the memory 12, and is taken as the set value of the signal voltage of the photomultiplier tube 4. Then, test measurement is performed in a state where control of bringing the signal voltage of the photomultiplier tube 4 close to the set value is performed, by atomizing the sample at the atomizing unit 2 and detecting, by the photomultiplier tube 4, measurement light which has passed through the generated atomic vapor.

Although not particularly restricted, the preset value is desirably a value of 50% to 70% of the maximum value of the signal voltage of the photomultiplier tube 4. In the case where the maximum value of the signal voltage of the photomultiplier tube 4 is 2.5 V, the preset value may be set to 1.5 V, for example.

The signal voltage optimization processing unit $7b$ optimizes the set value of the signal voltage of the photomultiplier tube 4 corresponding to a sample based on the signal voltage of the photomultiplier tube 4 at the time of test measurement of the sample. Specifically, if, as a result of the test measurement of the sample, it is determined that the signal voltage of the photomultiplier tube 4 may be saturated at the time of actual measurement, the set value of the signal voltage of the photomultiplier tube 4 corresponding to the sample is set to a lower value.

In this manner, according to the present embodiment, by performing test measurement of a sample, the set value of the signal voltage of the photomultiplier tube 4 corresponding to the sample may be optimized based on the signal voltage of the photomultiplier tube 4 at the time of the test measurement. That is, the set value of the signal voltage of the photomultiplier tube 4 corresponding to a sample may be optimized through test measurement using the actual sample.

Thus, even in a case where the amount of light emission of the sample itself or of the structure of the atomizing unit 2 is unexpectedly great, the set value of the signal voltage of the photomultiplier tube 4 corresponding to the sample may be set to a value according to which the signal voltage is not saturated at the time of actual measurement. Accordingly, saturation of the signal voltage of the photomultiplier tube 4 at the time of measurement may be effectively prevented.

In the present embodiment, the memory 12 configures a signal voltage storage unit that stores, in association with a sample, a set value of the signal voltage of the photomultiplier tube 4 which has been optimized by the signal voltage optimization processing unit 7b. By storing an optimized set value of the signal voltage of the photomultiplier tube 4 in association with a sample as described above, at the time of performing measurement of the same sample, measurement may be performed by reading the set value. Then, the efficiency of measurement may be increased, and also, saturation of the signal voltage of the photomultiplier tube 4 at the time of measurement may be effectively prevented.

Figure 2:
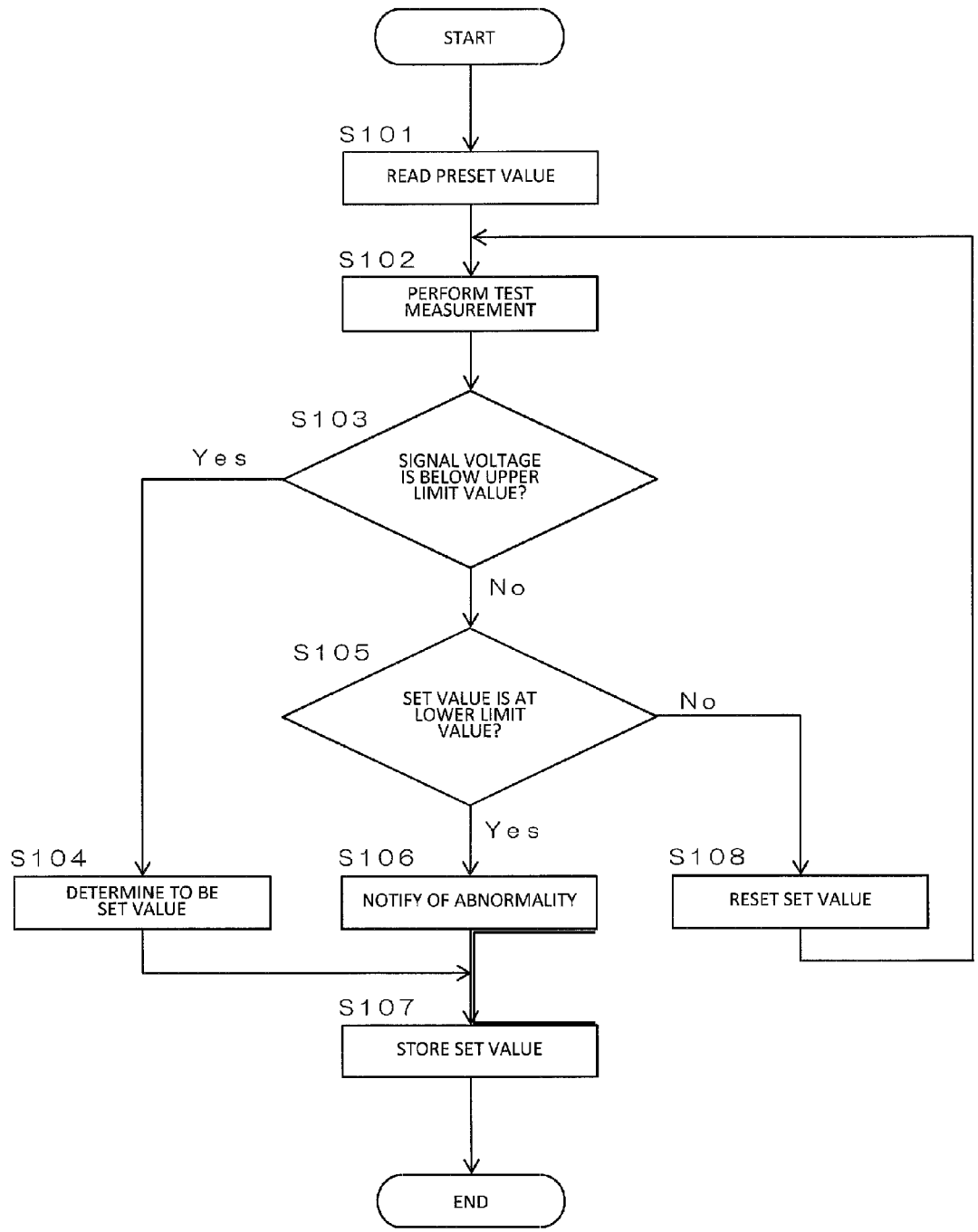
FIG. 2 is a flow chart showing an example of processing by a control unit at the time of test measurement.

FIG. 2 is a flow chart showing an example of processing by the control unit 7 at the time of test measurement. In the present embodiment, a value higher than the preset value is set in advance as the upper limit value of the signal voltage of the photomultiplier tube 4, and a value lower than the preset value is set in advance as the lower limit value of the set value of the signal voltage of the photomultiplier tube 4.

Additionally, the upper limit value of the signal voltage of the photomultiplier tube 4 refers to the maximum voltage at which the signal voltage is saturated and measurement cannot be normally performed, for example. Also, the lower limit value of the set value of the signal voltage of the photomultiplier tube 4 refers to the minimum voltage which is such a value that if the set value is set to a value lower than that, the S/N ratio at the time of measurement is too low and measurement cannot be performed normally, for example.

At the time of performing test measurement of a sample, first, a preset value of the signal voltage of the photomultiplier tube 4 is read from the memory 12 (step S101). Then, test measurement of a sample is performed with the preset value taken as the set value of the signal voltage of the photomultiplier tube 4 (step S102).

In the case where the signal voltage of the photomultiplier tube 4 at the time of the test measurement of the sample is below the upper limit value (Yes in step S103), the preset value is determined to be the set value of the signal voltage of the photomultiplier tube 4 corresponding to the sample (step S104). At this time, the preset value is stored in the memory 12 in association with the sample, as the set value of the signal voltage of the photomultiplier tube 4 (step S107).

On the other hand, in the case where the signal voltage of the photomultiplier tube 4 at the time of the test measurement of the sample is at or above the upper limit value (No in step S103), whether or not the set value of the signal voltage of the photomultiplier tube 4 has reached the lower limit value is determined (step S105). At this point, the set value of the signal voltage of the photomultiplier tube 4 is the preset value, which is a value higher than the lower limit value, and thus, the set value of the signal voltage of the photomultiplier tube 4 has not reached the lower limit value (No in step S105).

In this case, the set value of the signal voltage of the photomultiplier tube 4 is reset to a lower value (for example, a value that is one step lower) (step S108), and the test measurement of the sample is performed again using the set value (step S102). If, as a result, the signal voltage of the photomultiplier tube 4 at the time of the test measurement of the sample is below the upper limit value (Yes in step S103), the set value of the signal voltage of the photomultiplier tube 4 at this time is determined to be the set value of the signal voltage of the photomultiplier tube 4 corresponding to the sample (step S104), and this set value is stored in the memory 12 in association with the sample (step S107).

The test measurement of the sample (step S102) may be performed several times until the signal voltage of the photomultiplier tube 4 at the time of the test measurement is below the upper limit value (until Yes is achieved in step S103). In the case where the test measurement of the sample is performed several times in this manner, the set value of the signal voltage when the signal voltage of the photomultiplier tube 4 at the time of the test measurement falls below the upper limit value is determined to be the set value of the signal voltage of the photomultiplier tube 4 corresponding to the sample (step S104), and this set value is stored in the memory 12 in association with the sample (step S107).

However, if the set value of the signal voltage of the photomultiplier tube 4 that is reset reaches the lower limit value (Yes in step S105) before the signal voltage of the photomultiplier tube 4 at the time of the test measurement of the sample falls below the upper limit value (before Yes is achieved in step S103), the test measurement of the sample is ended. In this case, an abnormality notification is issued by a display on the display unit 11 (step S106), for example, and the set value of the signal voltage of the photomultiplier tube 4 that is set in the test measurement of the sample at the time is stored in the memory 12 in association with the sample (step S107).

In the present embodiment, steps S101, S102, and S108 in FIG. 2 constitute a test measurement execution processing step of performing test measurement of a sample. Steps S103, S104, and S105 constitute a signal voltage optimization processing step of optimizing the set value of the signal voltage of the photomultiplier tube 4 corresponding to a sample. Step S107 constitutes a signal voltage storing step of storing an optimized set value of the signal voltage of the photomultiplier tube 4 in association with a sample.

Step S106 constitutes an abnormality notification step of notifying an operator of an abnormal state. Incidentally, for example, a normality notification step of notifying an operator of normal completion in the case where the set value of the signal voltage of the photomultiplier tube 4 is normally determined in step S104 may be included without being restricted to the abnormality notification step. In this case, the normality notification may be issued by a display on the display unit 11, for example.

As described above, in the present embodiment, in the case where the signal voltage of the photomultiplier tube 4 is below the upper limit value at the time of test measurement of a sample where a preset value is taken as the set value of the signal voltage of the photomultiplier tube 4 (Yes in step S103), the preset value may be determined to be a value according to which the signal voltage of the photomultiplier tube 4 will not be saturated at the time of actual measurement, and be determined to be the set value corresponding to the sample (step S104).

On the other hand, in the case where the signal voltage of the photomultiplier tube 4 is at or above the upper limit value at the time of test measurement of a sample where the preset value is taken as the set value of the signal voltage of the photomultiplier tube 4 (No in step S103), the preset value may be determined to be a value according to which the signal voltage of the photomultiplier tube 4 will possibly be saturated, and be reset to a lower value (step S108). In the case where the set value of the signal voltage of the photomultiplier tube 4 is reset in the above manner, and the test measurement of the sample is performed several times, the set value of the signal voltage at the time of the signal voltage of the photomultiplier tube 4 falling below the upper limit value (at the time when Yes is achieved in step S103) may be determined to be a value according to which the signal voltage of the photomultiplier tube 4 will not be saturated at the time of actual measurement, and be determined to be the set value corresponding to the sample (step S104).

Also, in the case where the set value reaches the lower limit value without the signal voltage of the photomultiplier tube 4 falling below the upper limit value when the set value of the signal voltage of the photomultiplier tube 4 is reset and test measurement of the sample is performed several times (Yes in step S105), the test measurement of the sample may be ended. In such a case, conditions other than the signal voltage of the photomultiplier tube 4 (for example, atomization conditions) have to be re-examined, and thus, the test measurement of the sample is ended, and other appropriate measures may be taken.

Figure 3:
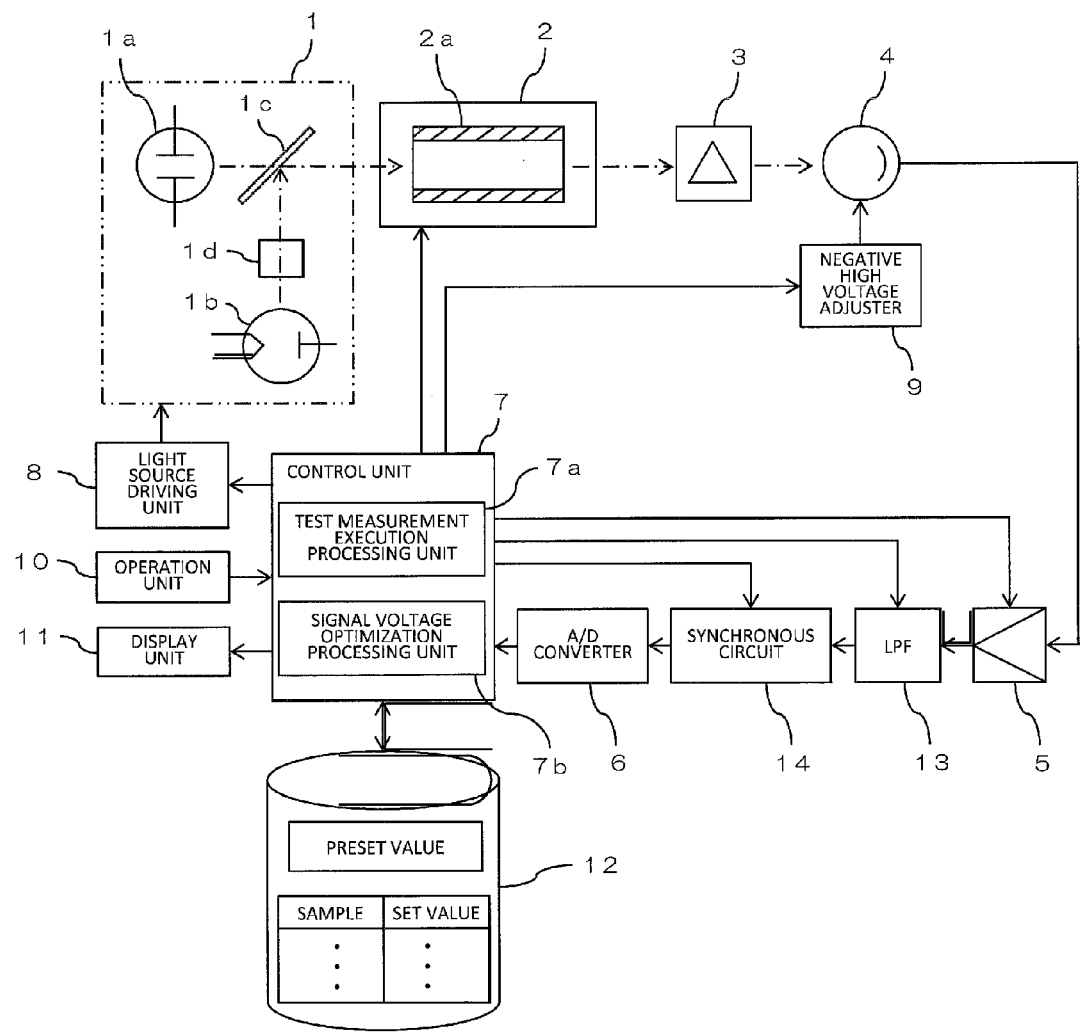
FIG. 3 is a diagram showing a configuration example of an atomic absorption spectrophotometer according to another embodiment.

FIG. 3 is a diagram showing a configuration example of an atomic absorption spectrophotometer according to another embodiment. This atomic absorption spectrophotometer is a furnace atomic absorption spectrophotometer, as in the embodiment described above, but is a dual light source atomic absorption spectrophotometer including, at the light source 1, a deuterium lamp (D2L) 1b for radiating light including a continuous spectrum, in addition to the hollow cathode lamp 1a.

This atomic absorption spectrophotometer is capable of performing so-called background correction using light from the deuterium lamp 1b. Structures other than that regarding the background correction are the same as the structures of the embodiment described above, and the same structures are denoted with the same reference signs in the drawing, and detailed description thereof is omitted.

A semitransparent mirror 1c is provided to the light source 1, and measurement light radiated from the hollow cathode lamp 1a passes through the semitransparent mirror 1c and enters the graphite tube 2a of the atomizing unit 2. On the other hand, light from the deuterium lamp 1b is reflected by the semitransparent mirror 1c, and enters the graphite tube 2a of the atomizing unit 2 on the same axis as the measurement light from the hollow cathode lamp 1a.

The hollow cathode lamp 1a and the deuterium lamp 1b are pulse-lighted under the control of the control unit 7 via the light source driving unit 8. The measurement light from the hollow cathode lamp 1a and the light from the deuterium lamp 1b are alternately detected by the photomultiplier tube 4 via the atomizing unit 2 and the spectroscope 3, and a time division multiplexed (TDM) signal is output from the photomultiplier tube 4.

An output signal from the photomultiplier tube 4 has the high frequency noise removed by a low-pass filter (LPF) 13 after being amplified by the amplifier 5, and is input to a synchronous circuit 14. At the synchronous circuit 14, an output signal of the photomultiplier tube 4 based on the measurement light from the hollow cathode lamp 1a and an output signal of the photomultiplier tube 4 based on the light from the deuterium lamp 1b are separated, and these output signals are input to the control unit 7 via the A/D converter 6.

Depending on the type of the sample, the measurement conditions or the like, the measurement light from the hollow cathode lamp 1a may undergo absorption (background absorption) other than the original absorption at the atomizing unit 2. According to the present embodiment, also in such a case, by calculating the difference between the output signal of the photomultiplier tube 4 based on the measurement light from the hollow cathode lamp 1a and the output signal of the photomultiplier tube 4 based on the light from the deuterium lamp 1b, background correction may be performed, and the influence of background absorption may be eliminated.

The present invention may also be applied to the dual light source atomic absorption spectrophotometer as described above. However, in this case, the difference between the set value, of the signal voltage of the photomultiplier tube 4 based on the measurement light, which is optimized by test measurement and the signal voltage of the photomultiplier tube 4 based on the light from the deuterium lamp 1b is desirably smaller. Accordingly, in the present embodiment, a structure is adopted according to which a variable dimmer 1d is provided to the light source 1 and the amount of light from the deuterium lamp 1b is adjusted, thereby making it possible to reduce the difference.

In the embodiment described above, a concrete example as shown in FIG. 2 is described as the method for optimizing the set value of the signal voltage of the photomultiplier tube 4. However, the method for optimizing the set value is not restricted to such a concrete example, and the set value may be optimized in various other modes.

For example, in the case where the signal voltage of the photomultiplier tube 4 at the time of test measurement of a sample is at or above the upper limit value (No in step S103), a configuration may be adopted according to which the set value is reset by an operator operating the operation unit 10, instead of being limited to a configuration where the set value of the signal voltage of the photomultiplier tube 4 is automatically reset to a lower value (step S108).

The detector for detecting measurement light is not limited to the photomultiplier tube 4, and various other detectors may be adopted. Also, the light source for radiating the measurement light is not limited to the hollow cathode lamp 1a, and various other light sources may be adopted.

Also, the present invention is not limited to the furnace atomic absorption spectrophotometer, and may also be applied to, for example, a flame atomic absorption spectrophotometer that sprays a sample to a flammable gas and burns the mixture gas thereby heating and atomizing the sample, and that measures the absorbance of the sample by causing measurement light to pass through the generated atomic vapor.

DESCRIPTION OF REFERENCE SIGNS 1 light source
1a hollow cathode lamp
1b deuterium lamp
1c semitransparent mirror
1d variable dimmer
2 atomizing unit 2a graphite tube
3 spectroscope
4 photomultiplier tube
5 amplifier
6 A/D converter
7 control unit
7a test measurement execution processing unit
7b signal voltage optimization processing unit
8 light source driving unit
9 negative high voltage adjuster
10 operation unit
11 display unit
12 memory
13 low-pass filter
14 synchronous circuit

The invention claimed is:

1. An atomic absorption spectrophotometer for causing measurement light to pass through atomic vapor generated by heating and atomizing a sample and detecting the measurement light with a detector to measure absorbance of the sample, the atomic absorption spectrophotometer comprising:

a test measurement execution processing unit implemented by a computer executing programs and configured to perform test measurement of the sample in a state where a preset value is taken as a set value of a signal voltage of the detector, a signal voltage optimization processing unit implemented by the computer executing programs and configured to optimize, based on the signal voltage of the detector at a time of the test measurement of the sample, the set value of the signal voltage of the detector corresponding to the sample, without predicting a future value of the signal voltage; and a signal voltage storage unit implemented by a memory for storing, in association with the sample, the set value of the signal voltage of the detector optimized by the signal voltage optimization processing unit.

2. The atomic absorption spectrophotometer according to claim 1, wherein, in a case where the signal voltage of the detector at a time of the test measurement of the sample is below an upper limit value, the signal voltage optimization processing unit determines the preset value to be the set value of the signal voltage of the detector corresponding to the sample.

3. The atomic absorption spectrophotometer according to claim 1, wherein, in a case where the signal voltage of the detector at a time of the test measurement of the sample is at or above an upper limit value, the test measurement execution processing unit resets the set value of the signal voltage of the detector to a lower value, and performs again the test measurement of the sample, and wherein, in a case where the test measurement of the sample is performed several times, the signal voltage optimization processing unit determines the set value of the signal voltage when the signal voltage of the detector falls below the upper limit value to be the set value of the signal voltage of the detector corresponding to the sample.

4. The atomic absorption spectrophotometer according to claim 3, wherein, in a case where the set value of the signal voltage of the detector that is reset reaches a lower limit value, the test measurement execution processing unit determines that there is an abnormality and ends the test measurement of the sample.

5. A signal voltage optimization method of an atomic absorption spectrophotometer, the method being for optimizing a set value of a signal voltage of a detector in the atomic absorption spectrophotometer for causing measurement light to pass through atomic vapor generated by heating and atomizing a sample and detecting the measurement light by the detector to measure absorbance of the sample, the method comprising:

a test measurement execution processing step of performing test measurement of the sample in a state where a preset value is taken as the set value of the signal voltage of the detector, a signal voltage optimization processing step of optimizing, based on the signal voltage of the detector at a time of the test measurement of the sample, the set value of the signal voltage of the detector corresponding to the sample, without predicting a future value of the signal voltage; and a signal voltage storage step of storing, in association with the sample, the set value of the signal voltage of the detector optimized in the signal voltage optimization processing step.

6. The signal voltage optimization method of the atomic absorption spectrophotometer according to claim 5, wherein, in the signal voltage optimization processing step, in a case where the signal voltage of the detector at a time of the test measurement of the sample is below an upper limit value, the preset value is determined to be the set value of the signal voltage of the detector corresponding to the sample.

7. The signal voltage optimization method of the atomic absorption spectrophotometer according to claim 5, wherein, in the test measurement execution processing step, in a case where the signal voltage of the detector at a time of the test measurement of the sample is at or above an upper limit value, the set value of the signal voltage of the detector is reset to a lower value, and the test measurement of the sample is performed again, and wherein, in the signal voltage optimization processing step, in a case where the test measurement of the sample is performed several times, the set value of the signal voltage when the signal voltage of the detector falls below the upper limit value is determined to be the set value of the signal voltage of the detector corresponding to the sample.

8. The signal voltage optimization method of the atomic absorption spectrophotometer according to claim 7, wherein, in the test measurement execution processing step, in a case where the set value of the signal voltage of the detector that is reset reaches a lower limit value, it is determined that there is an abnormality, and the test measurement of the sample is ended.

9. An atomic absorption spectrophotometer comprising:

a light source configured to generate measurement light;

an atomizer configured to heat a sample and generate vapor, wherein the atomizer receives the measurement light;

a spectroscope configured to receive the measurement light that passes through the atomizer and measure absorbance of the sample;

a photomultiplier and a voltage adjuster configured to control a signal voltage of the photomultiplier;

a controller configured to:

perform test measurement of the sample in a state where a preset value is taken as a set value of a signal voltage of the photomultiplier, and optimize, based on the signal voltage of the photomultiplier at a time of the test measurement of the sample, the set value of the signal voltage of the photomultiplier corresponding to the sample, without predicting a future value of the signal voltage, wherein the atomic absorption spectrophotometer further comprises a memory for storing, in association with the sample, the set value of the signal voltage of the photomultiplier optimized by the controller.

10. The atomic absorption spectrophotometer according to claim 9, wherein when the signal voltage of the photomultiplier at a time of the test measurement of the sample is below an upper limit value, the controller determines the preset value to be the set value of the signal voltage of the photomultiplier corresponding to the sample, and wherein when the signal voltage of the photomultiplier at a time of the test measurement of the sample is at or above an upper limit value, the controller resets the set value of the signal voltage of the photomultiplier to a lower value, and performs the test measurement of the sample again.

* * * * *